United States Patent
Fabien

(10) Patent No.: US 10,668,216 B2
(45) Date of Patent: Jun. 2, 2020

(54) AUTO-INJECTOR

(71) Applicant: APTAR FRANCE SAS, Le Neubourg (FR)

(72) Inventor: David Fabien, Saint Quay Perros (FR)

(73) Assignee: APTAR FRANCE SAS, Le Neubourg (FR)

(*) Notice: Subject to any disclaimer, the term of this patent is extended or adjusted under 35 U.S.C. 154(b) by 451 days.

(21) Appl. No.: 15/038,785

(22) PCT Filed: Nov. 21, 2014

(86) PCT No.: PCT/FR2014/052997
§ 371 (c)(1),
(2) Date: May 24, 2016

(87) PCT Pub. No.: WO2015/075399
PCT Pub. Date: May 28, 2015

(65) Prior Publication Data
US 2016/0375195 A1 Dec. 29, 2016

(30) Foreign Application Priority Data
Nov. 25, 2013 (FR) ...................... 13 61557

(51) Int. Cl.
*A61M 5/20* (2006.01)
*A61M 5/32* (2006.01)

(52) U.S. Cl.
CPC ............ *A61M 5/20* (2013.01); *A61M 5/3272* (2013.01); *A61M 2005/208* (2013.01);
(Continued)

(58) Field of Classification Search
CPC ........ A61M 5/20; A61M 5/24; A61M 5/3271; A61M 5/3272; A61M 2005/2013; A61M 2005/208; A61M 2005/2073
See application file for complete search history.

(56) References Cited

U.S. PATENT DOCUMENTS

2008/0228147 A1* 9/2008 David-Hegerich ... A61M 5/326
604/198
2009/0024093 A1* 1/2009 Carrel ................... A61M 5/326
604/198
(Continued)

FOREIGN PATENT DOCUMENTS

EP 2 468 328 A1 6/2012
FR 2 884 722 A 10/2006
(Continued)

OTHER PUBLICATIONS

International Preliminary Report on Patentability, dated Jun. 23, 2016, from the International Bureau in counterpart International application No. PCT/FR2014/052997.
(Continued)

*Primary Examiner* — Lauren P Farrar
*Assistant Examiner* — James D Ponton
(74) *Attorney, Agent, or Firm* — Sughrue Mion, PLLC

(57) ABSTRACT

An autoinjector having a body (1) and an actuator sleeve (10) having a first projecting position before actuation and a second projecting position after actuation. The actuator sleeve or the body has a flexible tab (110) that deforms laterally when the actuator sleeve moves from its first projecting position to its actuated position, then from its actuated position to return to its second projecting position. The other of the actuator sleeve and the body has an initial zone (102), an intermediate zone (105), and a final reception zone (106) co-operating with the flexible tab in the first projecting position, actuated position, and second projecting position, respectively. The final reception zone is offset laterally from the initial zone. A deformable axial wall (1020) deforms allowing the flexible tab to pass from the initial zone to the intermediate zone and guides it from the intermediate zone to the final reception zone.

14 Claims, 3 Drawing Sheets

(52) U.S. Cl.
CPC ........... *A61M 2005/2013* (2013.01); *A61M 2005/2073* (2013.01); *A61M 2205/581* (2013.01)

(56) References Cited

U.S. PATENT DOCUMENTS

| | | | |
|---|---|---|---|
| 2011/0319833 A1* | 12/2011 | Chun | A61M 5/326 604/198 |
| 2012/0316508 A1* | 12/2012 | Kirchhofer | A61M 5/31553 604/198 |
| 2013/0211338 A1* | 8/2013 | Roberts | A61M 5/326 604/198 |
| 2013/0324925 A1 | 12/2013 | Brereton et al. | |

FOREIGN PATENT DOCUMENTS

| | | |
|---|---|---|
| FR | 2 990 862 A1 | 11/2013 |
| WO | 2009/040602 A1 | 4/2009 |
| WO | 2012/000832 A1 | 1/2012 |

OTHER PUBLICATIONS

International Search Report for PCT/FR2014/052997 dated Feb. 4, 2015.

\* cited by examiner

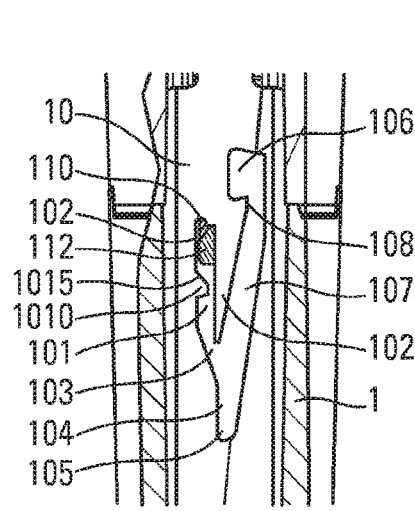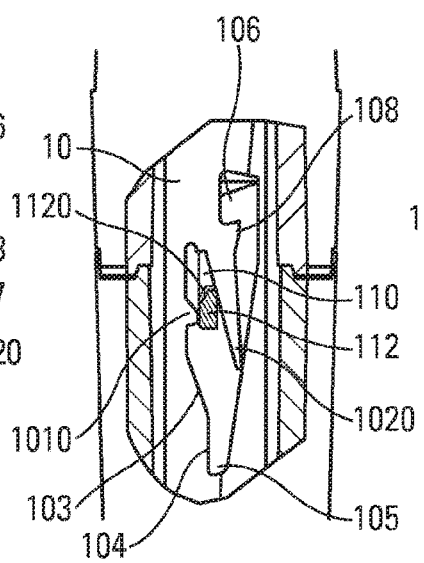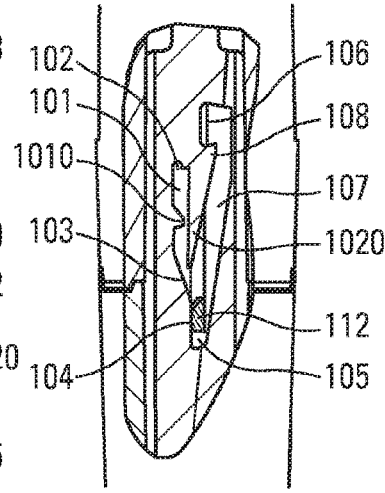
Fig. 8　　　　Fig. 9　　　　Fig. 10
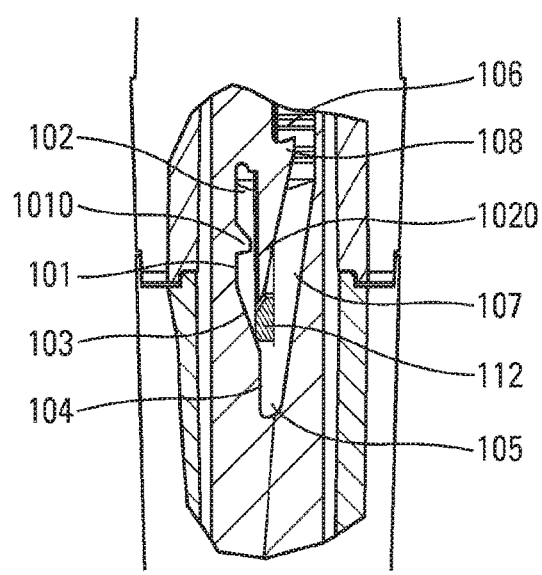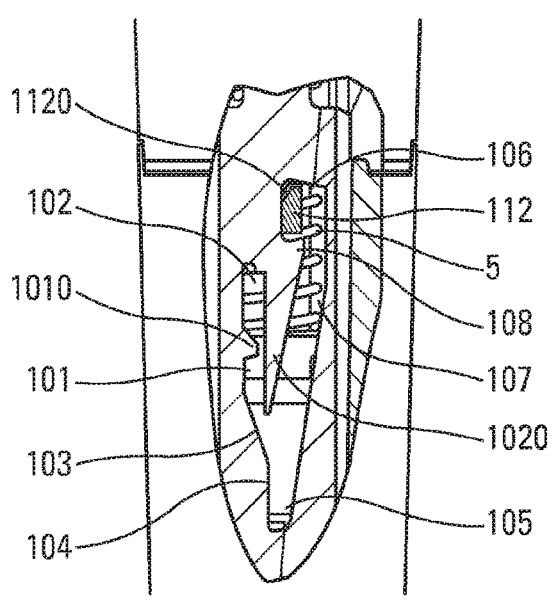
Fig. 11　　　　Fig. 12

AUTO-INJECTOR

CROSS REFERENCE TO RELATED APPLICATIONS

This application is a National Stage of International Application No. PCT/FR2014/052997 filed Nov. 21, 2014, claiming priority based on French Patent Application No. 1361557 filed Nov. 25, 2013, the contents of all of which are incorporated herein by reference in their entirety.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic.

Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they all present a certain number of drawbacks.

Thus, in order to avoid the autoinjector being triggered accidentally, e.g. during transport or during storage, the devices should include reliable locking means. In addition, when a user wishes to use the autoinjector and unlocks the device, e.g. by removing the cap, the device should not be triggered accidentally, but only when the user actually wishes it, i.e. when the user applies it against the part of the body where injection is to be performed. Unfortunately, in particular when the people using an autoinjector are elderly or handicapped people, the user may drop the device when it is to be used. In such circumstances, it is desirable that the autoinjector does not trigger itself. It is thus important to provide a reliable trigger lock. Equally, use of the autoinjector must not become too difficult, as this would prevent weak people from using it. It is thus difficult to find a good compromise between the safety of locking, and the ease with which the autoinjector can be used and actuated. An object of the present invention is to satisfy this problem.

Furthermore, in order to avoid any risk of injury after using the device, the autoinjector should include a needle safety device that avoids the needle remaining visible after the device has been used. Obviously, the safety device should also be reliable and not be released too easily. It should also be functional even when the user actuates the autoinjector poorly, e.g. when the user removes it too soon from the body, before the end of injection.

Documents WO 2012/045833, FR 2 884 722, WO 96/32974, and WO 2012/000832 describe prior-art devices.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable in use, that is safe and that prevents any risk of injury, and that is simple and inexpensive to manufacture and to assemble.

The present invention thus provides an autoinjector comprising a body that is adapted to receive a reservoir, said reservoir containing fluid and including a piston and a needle, such as a pre-filled syringe, said autoinjector further comprising an actuator sleeve that includes a contact end for coming into contact with the user's body, said actuator sleeve being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector; one of said actuator sleeve and of said body including a flexible tab that is adapted to deform laterally relative to said actuator sleeve and/or relative to said body when said actuator sleeve is moved from its first projecting position to its actuated position, then from its actuated position to return to its second projecting position, the other of said actuator sleeve and of said body including an initial zone that co-operates with said flexible tab in said first projecting position, an intermediate zone that co-operates with said flexible tab in said actuated position, and a final reception zone that co-operates with said flexible tab in said second projecting position, said final reception zone being offset, at least laterally, from said initial zone, a deformable axial wall being adapted to deform elastically so as to allow said flexible tab to pass from said initial zone to said intermediate zone, said deformable axial wall, in its non-deformed position, then being adapted to guide said flexible tab from said intermediate zone to said final reception zone.

Advantageously, said flexible tab is deformed laterally when said actuator sleeve is moved from its first projecting position, before actuation, to its actuated position, and/or said flexible tab is deformed laterally when said actuator sleeve is moved from its actuated position to its second projecting position, at the end of use.

Advantageously, said actuator sleeve includes at least one initial groove that connects said initial zone to said intermediate zone, said initial groove including said deformable axial wall.

Advantageously, said initial groove includes a shoulder that projects laterally into said initial groove.

Advantageously, said shoulder is arranged facing said deformable axial wall.

Advantageously, said shoulder includes a sloping wall that faces towards said initial zone, said sloping wall deforming said flexible tab laterally, in such a manner that said flexible tab deforms said deformable axial wall.

Advantageously, said initial groove is substantially axial and is connected to said intermediate zone via a sloping second groove and/or via an axial third groove.

Advantageously, said final reception zone is connected to said intermediate zone via a final groove, an axial shoulder being provided between said final reception zone and said final groove, said flexible tab being adapted to slide in said final groove when said actuator sleeve returns from its actuated position to its second projecting position, said flexible tab becoming snap-fastened below said axial shoulder when said actuator sleeve reaches its second projecting position after use, thereby locking said actuator sleeve relative to said body.

Advantageously, said final reception zone is offset axially relative to said initial zone.

Advantageously, said final groove slopes and includes said deformable axial wall.

Advantageously, said snap-fastening of said flexible tab in said final reception zone generates a sound, such as a click.

Advantageously, said elastic deformation of said deformable axial wall generates a sound, such as a click.

Advantageously, said flexible tab includes a head that slides in said initial and final grooves between said initial, intermediate, and final-reception zones, said head including a front end wall that slopes at least in part, and that is adapted to co-operate with a sloping end of said deformable axial wall so as to guide said head into said final groove when said actuator sleeve returns from its actuated position to its second projecting position.

These characteristics and advantages, and others, of the present invention appear more clearly from the following detailed description, given by way of non-limiting example, and with reference to the accompanying drawings, in which:

FIGS. 8 to 12 are diagrammatic and fragmentary views showing, in detail, the lock during various sequences of use of the autoinjector in a second advantageous embodiment.

Figure 1:
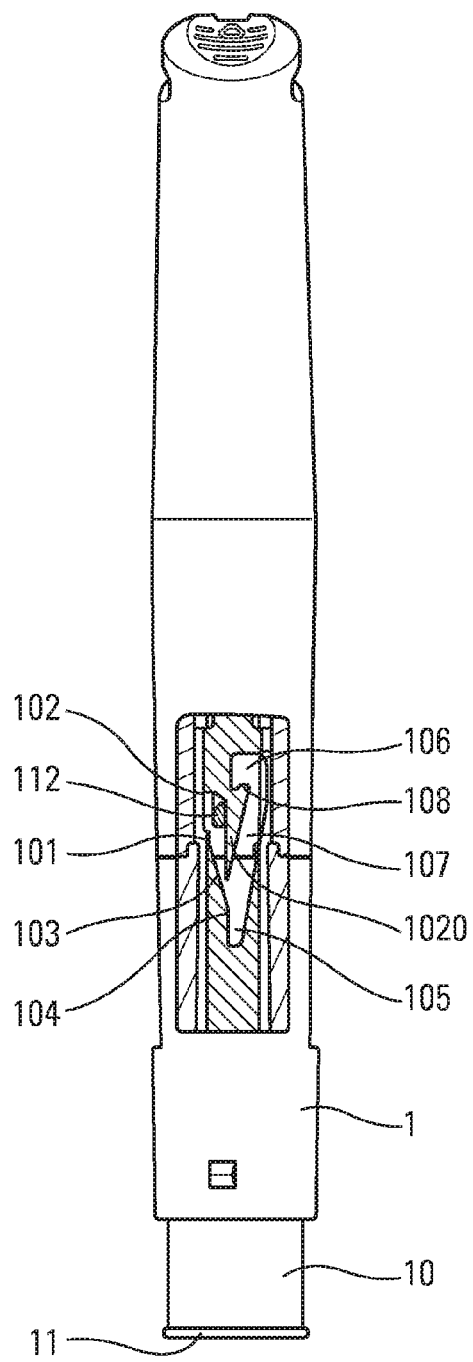
FIG. 1 is a partially cut-away diagrammatic view of an autoinjector in an advantageous embodiment.

The autoinjector shown in FIG. 1 comprises a body 1 in which an actuator sleeve 10 slides axially, the actuator sleeve 10 having a bottom end 11 (in the orientation in FIG. 1) that is for coming into contact with the body of the patient around the injection zone. In known manner, the body 1 contains a reservoir containing the fluid to be injected, a needle through which the fluid is dispensed, a piston that is adapted to move in said reservoir so as to perform the dispensing, and an automatic injection system that is adapted to co-operate with said piston so as to move it. These elements, conventional in an autoinjector, are not shown in the drawings for the sake of clarity, and they could be made of any appropriate material, in particular being similar to those described in documents FR 2 990 862, FR 2 990 863, FR 2 990 864, FR 2 990 865, FR 2 990 866, FR 2 990 867, FR 2 990 868, FR 2 990 869, and FR 2 990 870. Typically, the reservoir may be a conventional pre-filled syringe.

Before actuation, the actuator sleeve 10 is in a first projecting position in which it surrounds the needle. During actuation, the actuator sleeve 10 slides inside the body 1 towards an actuated position, so as to expose the needle and enable pricking, and injection of the fluid. After injection, the actuator sleeve 10 returns into a second projecting position in which it is once again arranged around the needle, so as to avoid any risk of injury with said needle. The actuator sleeve 10 is advantageously urged towards its projecting positions by a spring 5 that may be of any type.

The actuator sleeve 10 includes an initial groove 101, advantageously an axial groove, that extends from an initial zone 102 to an intermediate zone 105. Said initial groove 101 includes an elastically-deformable axial wall 1020. Advantageously, a second groove 103, preferably a sloping groove, and/or a third groove 104, advantageously an axial groove, connect said initial groove 101 to said intermediate zone 105. Said actuator sleeve 10 also includes a final reception zone 106 that is offset, at least laterally, relative to said initial zone 102, and that is connected to said intermediate zone 105 via a final groove 107, advantageously a sloping groove. An axial shoulder 108 is provided between said final reception zone 106 and said final groove 107.

The body 1 includes a tab 110 that is laterally flexible, i.e. it deforms in the peripheral direction of the body. The flexible tab 110 advantageously includes a head 112 that co-operates with the grooves and shoulders of the actuator sleeve 10, as described below.

More particularly, FIGS. 2 to 7 show the operation of the lock formed between the actuator sleeve 10 and the body 1.

Figure 2:
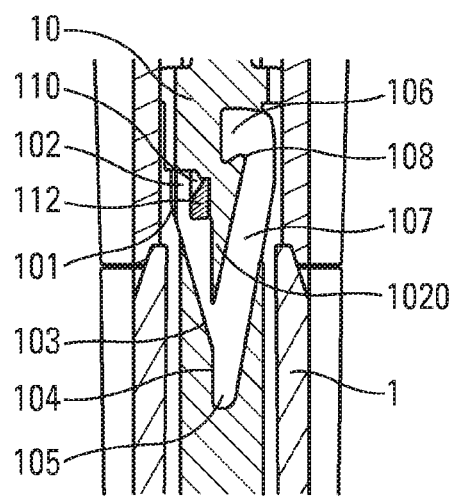
FIGS. 2 to 7 are diagrammatic and fragmentary views showing, in detail, the lock during various sequences of use of the FIG. 1 autoinjector.
Figure 3:
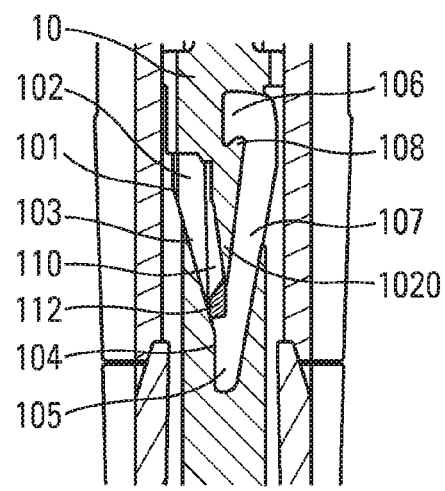

FIG. 2 shows the start position, i.e. when the user begins to use the autoinjector. In FIG. 2, it can be seen that the head 112 of the flexible tab 110 is arranged in said initial zone 102 of said initial groove 101. When the actuator sleeve 10 slides into the body 1, said head 112 of the flexible tab 110 slides inside said initial groove 101. When the head 112 reaches the position in FIG. 3, in which it co-operates on one side with the second groove 103 and on the other side with the deformable axial wall 1020, it deforms said deformable axial wall 1020 laterally, so as to be able to continue its actuation stroke. The deformation of the deformable axial wall 1020 enables the head 112 of the flexible tab 110 to pass into the intermediate zone 105, in particular through the axial third groove 104. In addition, when said deformable axial wall 1020 is fully deformed, it may generate a sound, such as a click, so as to signal to the user that injection is about to begin.

Figure 4:
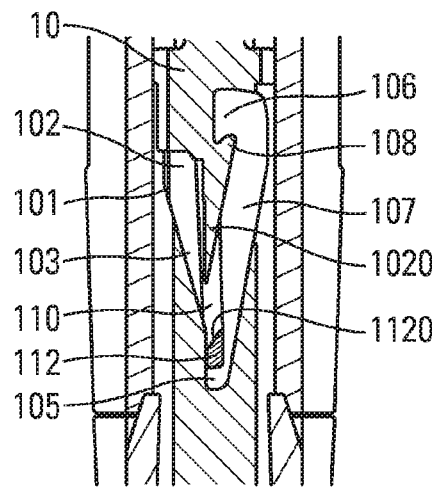

In the position shown in FIG. 4, the actuator sleeve 10 has reached its actuated position in which the needle has penetrated into the injection zone of the patient as far as the injection position, and in which said actuator sleeve 10 is capable of actuating the injection system. In this actuated position of the actuator sleeve 10, the head 112 of the flexible tab 110 is in the intermediate zone 105. In this position, the deformable axial wall 1020 has returned elastically to its non-deformed position, such that said intermediate zone 105 is connected to said final reception zone 106 via said sloping final groove 107.

Figure 5:
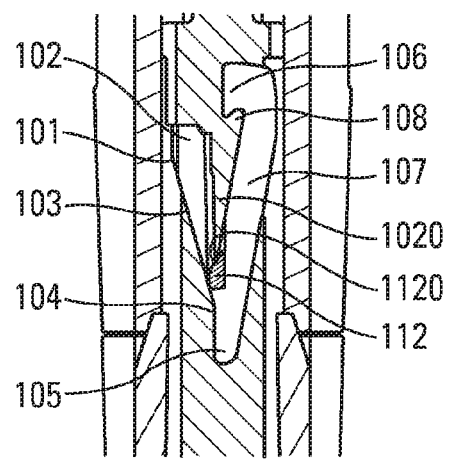

When said actuator sleeve 10 returns from its actuated position to its second projecting position under the effect of the spring 5, said head 112 of the flexible tab 110 slides into said sloping final groove 107. FIG. 5 is a diagram showing that the flexible tab 110, in particular the head 112, can no longer return into said initial groove 101 as a result of the deformable axial wall 1020 that prevents the passage of said head 112. Advantageously, said head 112 includes a front wall 1120 that slopes at least in part, and that co-operates with the end of said deformable axial wall 1020, so as to guide said head into the sloping final groove 107, as can be seen in FIG. 5. Thus, the deformable axial wall 1020 forms an integral part of the cam, formed by the final groove 107, that guides the flexible tab 110 towards the final reception zone 106.

Figure 6:
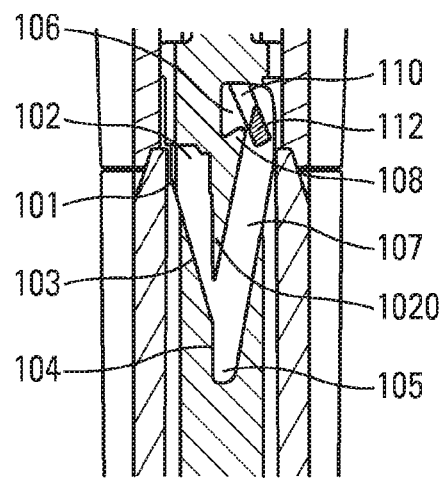
Figure 7:
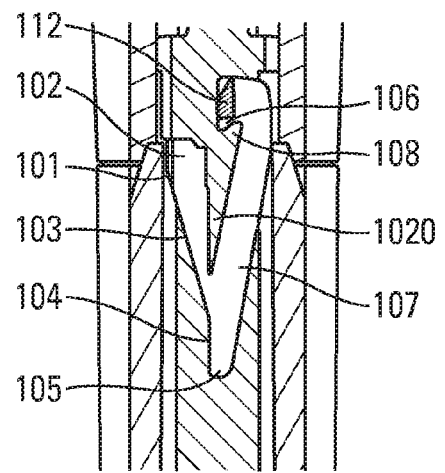

When said actuator sleeve 10 reaches its second projecting position after use, said head 112 becomes snap-fastened in said final reception zone 106 below said axial shoulder 108, thereby locking said actuator sleeve 10 relative to said body 1. From this locked position, said actuator sleeve 10 can no longer be moved towards its actuated position, as a result of the abutment formed between the head 112 of the flexible tab 110 and the axial shoulder 108. The lateral deformation of the flexible tab 110 during actuation, in particular in the sloping final groove 107 as shown in FIG. 6, causes the head 112 to snap-fasten resiliently and automatically below the axial shoulder 108 when the head 112 arrives in said final reception zone 106, as shown in FIG. 7. The safety device is thus in its locked final position. Thus, the needle is completely protected after use, and the user can no longer use the autoinjector or be injured by the needle. The snap-fastening in the final reception zone 106 may generate a sound, such as a click, so as to inform the user that the locked final position has been reached.

FIGS. 8 to 12 show a second advantageous embodiment of the invention that is very similar to the above described first embodiment. The only difference is that the initial groove 101 includes a shoulder 1010 that projects laterally into said initial groove 101, said shoulder 1010 preferably including a sloping wall 1015 that faces towards said initial zone 102.

Advantageously, the shoulder 1010 is provided facing said elastically-deformable axial wall 1020. When the head 112 reaches the sloping wall 1015 of the shoulder 1010 in the initial groove 101, said sloping wall 1015 co-operates with said head 112. The shoulder 1010 thus deforms the flexible tab 110 laterally. This in turn laterally deforms the deformable axial wall 1020, as can be seen in FIG. 9. The shoulder 1010 thus forms a hard point at the beginning of the actuation stage, which should be overcome in order to enable the autoinjector to be actuated. In particular, the hard point combines the deformation of the flexible tab 110 and the deformation of the deformable axial wall 1020, and in this second embodiment, the force exerted by the user on the actuator sleeve 10 should be sufficient to enable both deformations to be achieved. Energy thus accumulates and is released when the head 112 of the flexible tab 110 passes beyond the shoulder 1010. This guarantees that the actuation stroke is completed, with the head of the flexible tab passing into the intermediate zone 105, in particular through the sloping second groove 103 and the axial third groove 104.

Both of the above-mentioned variants for locking the actuator sleeve are particularly effective and reliable, while being robust and easy, and thus inexpensive, to mold and to assemble. In particular, they comprise only two parts, the actuator sleeve 10 and the body 1.

Naturally, the shapes of the grooves, their dimensions, and their slopes may be modified as a function of the needs of and the characteristics desired for the needle safety device. In particular, the initial groove may be axial or sloping. It may lead directly to the intermediate zone, without there being second and third grooves. With a sloping initial groove, the final groove could be axial or also sloping. Other variants may also be envisaged.

It should be observed that the above-described means could be achieved in inverted manner, i.e. the body 1 could include the various grooves 101, 103, 104, and 107, the shoulders 1010 and 108, and the deformable axial wall 1020, and the actuator sleeve 10 could include the flexible tab 110. Naturally, in this configuration, the shapes and orientations of said grooves would be adapted accordingly.

Although the present invention is described above with reference to two advantageous embodiments, naturally various modifications can be applied thereto by the person skilled in the art, without going beyond the ambit of the present invention, as defined by the accompanying claims.

The invention claimed is:

1. An autoinjector comprising;
   a body adapted to receive a reservoir, said reservoir containing fluid and including a piston and a needle;
   an actuator sleeve that includes a contact end for coming into contact with a user at an injection site, said actuator sleeve being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector;
   one of said actuator sleeve and of said body including a flexible tabadapted to deform laterally in a first direction relative to said actuator sleeve and/or relative to said body when said actuator sleeve is moved from the first projecting position to the actuated position, and from the actuated position to return to the second projecting position, and the flexible tab being adapted to deform laterally in a second direction, opposite to the first direction, when the actuator sleeve arrives in the second projecting position;
   the other of said actuator sleeve and of said body including an initial zone that co-operates with said flexible tab in said first projecting position, wherein the initial zone is a zone where the flexible tab is located in a rest position before start of the actuation of the autoinjector, an intermediate zone that co-operates with said flexible tab in said actuated position, and a final reception zone that co-operates with said flexible tab in said second projecting position, said final reception zone being offset, at least laterally, from said initial zone;
   wherein a deformable axial wall is adapted to deform elastically so as to allow said flexible tab to pass from said initial zone to said intermediate zone, said deformable axial wall, in a non-deformed position, then being adapted to guide said flexible tab from said intermediate zone to said final reception zone;
   wherein said actuator sleeve includes at least one initial groove that connects said initial zone to said intermediate zone, said initial groove including said deformable axial wall;
   wherein said initial groove includes a shoulder that projects laterally into said initial groove;
   wherein said shoulder is arranged facing said deformable axial wall; and
   wherein said shoulder includes a sloping wall that faces towards said initial zone, said sloping wall deforming said flexible tab laterally, in such a manner that said flexible tab deforms said deformable axial wall.

2. An autoinjector according to claim 1, wherein said flexible tab is deformed laterally when said actuator sleeve is moved from its first projecting position, before actuation, to its actuated position, and/or said flexible tab is deformed laterally when said actuator sleeve is moved from its actuated position to its second projecting position, at an end of use.

3. An autoinjector according to claim 1, wherein said initial grooves substantially axial and is connected to said intermediate zone via a sloping second groove and/or via an axial third groove.

4. An autoinjector according to claim 1, wherein said final reception zone is connected to said intermediate zone via a final groove, an axial shoulder being provided between said final reception zone and said final groove, said flexible tab being adapted to slide in said final groove when said actuator sleeve returns from its actuated position to its second projecting position, said flexible tab becoming snap-fastened below said axial shoulder when said actuator sleeve reaches its second projecting position after use, thereby locking said actuator sleeve relative to said body.

5. An autoinjector according to claim 4, wherein said final reception zone is offset axially relative to said initial zone.

6. An autoinjector according to claim 4, wherein said final groove slopes and includes said deformable axial wall.

7. An autoinjector according to claim 4, wherein said snap-fastening of said flexible tab in said final reception zone generates a sound.

8. The autoinjector according to claim 7, wherein the sound generated is a click.

9. An autoinjector according to claim 1, wherein said elastic deformation of said deformable axial wall generates a sound.

10. The autoinjector according to claim 9, wherein the sound generated is a click.

11. An autoinjector according to claim 1, wherein said flexible tab includes a head that slides in said initial and final grooves between said initial, intermediate, and final reception zones, said head including a front end wall that slopes at least in part, and that is adapted to co-operate with a sloping end of said deformable axial wall so as to guide said head into said final groove when said actuator sleeve returns from its actuated position to its second projecting position.

12. The autoinjector according to claim 1, wherein the reservoir, fluid, piston and needle form a pre-filled syringe.

13. The autoinjector according to claim 1, wherein the actuator sleeve extends beyond a distal end of the needle in the first projecting position and the second projecting position.

14. The autoinjector according to claim 1, configured so that the flexible tab leaves the initial zone upon initial actuation of the autoinjector.

\* \* \* \* \*